US010591421B1

(12) United States Patent
Herrmann et al.

(10) Patent No.: US 10,591,421 B1
(45) Date of Patent: Mar. 17, 2020

(54) BEVERAGE BOTTLE HANDLING DEVICE FOR HANDLING BEVERAGE BOTTLES AND SIMILAR CONTAINERS IN A BEVERAGE BOTTLING OR CONTAINER FILLING PLANT

(71) Applicants: Jürgen-Peter Herrmann, Rosenheim (DE); Marius Michael Herrmann, Rosenheim (DE); Wolfgang Schorn, Hönningen (DE); Xiang Zhang, Wetter (DE)

(72) Inventors: Jürgen-Peter Herrmann, Rosenheim (DE); Marius Michael Herrmann, Rosenheim (DE); Wolfgang Schorn, Hönningen (DE); Xiang Zhang, Wetter (DE)

(73) Assignee: KHS GmbH, Dortmund (DE)

( * ) Notice: Subject to any disclaimer, the term of this patent is extended or adjusted under 35 U.S.C. 154(b) by 0 days.

(21) Appl. No.: 16/381,178

(22) Filed: Apr. 11, 2019

Related U.S. Application Data

(63) Continuation-in-part of application No. 15/245,674, filed on Aug. 24, 2016, now abandoned, which is a
(Continued)

(30) Foreign Application Priority Data

Feb. 25, 2014 (DE) .................. 10 2014 102 449

(51) Int. Cl.
*G01N 21/90* (2006.01)
*B65B 57/00* (2006.01)
(Continued)

(52) U.S. Cl.
CPC ............ *G01N 21/90* (2013.01); *B65B 57/00* (2013.01); *B67C 3/24* (2013.01); *B65G 29/00* (2013.01);
(Continued)

(58) Field of Classification Search
CPC ...... B65G 29/00; B65G 47/84; B65G 47/846; B65G 37/00; B65B 3/00; B65B 7/28;
(Continued)

(56) References Cited

U.S. PATENT DOCUMENTS 2,540,120 A * 2/1951 Jacobs ................. B67C 7/00
53/267
4,378,665 A * 4/1983 Crankshaw ............ B65C 9/02
198/346.2
(Continued)

FOREIGN PATENT DOCUMENTS

CN 101978291 A 2/2011
DE 100 65 290 7/2002
(Continued)

OTHER PUBLICATIONS

Lamprecht, J. "Visionsystem Automatisiert Das Abfuellen Von Getraenken" Elektrotechnik fuer die Automatisierung, Nov. 5, 1998 Vogel Business Media GmbH & Co.KG, vol. 80,Nr:11,pp. 146, 149, and English translation thereof.
(Continued)

*Primary Examiner* — James R Bidwell

(57) ABSTRACT

A beverage bottle checking arrangement is designed to check beverage bottles in a beverage bottle handling arrangement. The beverage bottle checking arrangement includes a single framework and checking devices mounted on the framework, which checking devices are designed to essentially simultaneously check characteristics of beverage bottles being moved through or past the framework.

16 Claims, 6 Drawing Sheets

Related U.S. Application Data continuation-in-part of application No. PCT/EP2015/053547, filed on Feb. 19, 2015.

(51) Int. Cl.
*B67C 3/24* (2006.01)
*G01N 33/00* (2006.01)
*B65G 29/00* (2006.01)

(52) U.S. Cl.
CPC ............... *B65G 2201/0244* (2013.01); *B65G 2203/044* (2013.01); *B65G 2812/14* (2013.01); *G01N 2033/0081* (2013.01)

(58) Field of Classification Search
CPC ....... B65B 65/003; B65B 35/44; B65B 35/46; B65B 3/04; B67B 3/02; B67B 3/064; B67B 3/006
USPC .......... 198/478.1, 480.1, 481.1; 53/267, 272, 53/276, 280, 282, 283
See application file for complete search history.

(56) References Cited

U.S. PATENT DOCUMENTS

| | | | |
|---|---|---|---|
| 5,373,683 A * | 12/1994 | Kronseder | B67B 3/02 53/267 |
| 7,010,900 B2 * | 3/2006 | Grossmann | A61L 2/208 134/169 R |
| 7,497,237 B2 * | 3/2009 | Till | A61L 2/22 141/11 |
| 7,832,185 B2 * | 11/2010 | Mastio | A61L 2/082 250/492.3 |
| 2004/0042004 A1 | 3/2004 | Lindner | |
| 2008/0291438 A1 | 11/2008 | Akkerman et al. | |
| 2009/0013645 A1 * | 1/2009 | Mastio | A61L 2/082 53/425 |
| 2011/0164131 A1 | 7/2011 | Wiemer et al. | |
| 2012/0113248 A1 | 5/2012 | Fiegler | |
| 2017/0348757 A1 * | 12/2017 | Kurosawa | B21D 51/30 |
| 2018/0194499 A1 * | 7/2018 | Zoni | B65G 47/84 |

FOREIGN PATENT DOCUMENTS

| | | |
|---|---|---|
| DE | 10 2008 034 744 A1 | 1/2010 |
| DE | 10 2008 062 385 | 7/2010 |
| DE | 10 2010 043 635 A1 | 5/2012 |
| EP | 1715328 A1 | 10/2006 |
| WO | WO 03/024859 A1 | 3/2003 |
| WO | WO 2008/104273 A1 | 9/2008 |
| WO | WO 2013/013771 A1 | 1/2013 |

OTHER PUBLICATIONS

Machine translation of WO 2008/104273 A1.
Machine translation of CN 101978291 A.
Machine translation of WO 2013/013771 A1.

* cited by examiner

BEVERAGE BOTTLE HANDLING DEVICE FOR HANDLING BEVERAGE BOTTLES AND SIMILAR CONTAINERS IN A BEVERAGE BOTTLING OR CONTAINER FILLING PLANT

BACKGROUND

1. Technical Field

The present application relates to a beverage bottle handling device for handling beverage bottles and similar containers in a beverage bottling or container filling plant.

2. Background Information

Background information is for informational purposes only and does not necessarily admit that subsequently mentioned information and publications are prior art.

As described in published European Patent EP1715328, it is common to drink beverages, such as beer, fruit juices, mineral water, or even soft drinks on a large scale, so they must be produced industrially. In order to be able to offer the consumer an always consistent and good product, it has proven to be particularly advantageous not only to carry out numerous checks during the actual production process, but also to subject the finished end product to a final inspection. The same applies analogously to other products bottled in glasses or bottles, such as oils, sauces, etc., so that the scope of the present application extends to the processing of such products, even if they are not explicitly mentioned below.

The term "end product" above is understood to mean the finished, filled, filled and labeled container. In the context of such a final inspection, the level, the correct fit of the labels, the surface labeling or surface quality of the final product, among other things, should be the subject of the inspection. In order to perform these inspection tasks, numerous solutions have been presented in the past, which are often so-called linear machines, since these treat the final product very gently due to their structural design and in particular do not damage the label equipment.

The present application relates to a container handling system having an inspection device for checking containers, and a container transport device for moving the container into a position where it can be inspected by the inspection device.

The present application relates to a compact inspection device for inspecting containers such as bottles in a container filling plant.

When a container is being transported through a container handling system with different work stations, it is usual for different features of the container to be checked. For example, the filling quantity of the container, the location of a label on the container, or also the position of a container closure or a logo on the container closure can be checked.

As described in published International Application WO2008104273, the container features in the context of the present application mean all optical and physical properties of the container to be examined, in particular its length, size, and diameter. In addition, the base, the location and attachment of additional structures, such as closures, labels, etc., fall under this. Also included in the generic term of the container features are the level of a filled liquid, the color of the bottle, the color of the filled liquid or the color of labels, any symbols, etc. Finally, within the framework of the measurement of the container features, the lateral surface of the container and/or the contour or shape of the container can also be measured and examined with regard to possible irregularities.

Such irregularities can be attributed, for example, to damage, imperfections in the container material, cracks, dents, etc., which are measured quantitatively in the context of the present application, like the container properties already described. This means that, for example, a crack in the container wall, the position of the label or a closure are geometrically determined exactly, for example, by assigning the crack a certain angular position of the usually rotationally symmetrical container and a height above a base surface. The position and orientation of the label is documented as part of the survey of the container features, for example, also by the swept angle range between transverse edges of the label and the height profile of the associated longitudinal edges relative to the base. In the examination of the container features, a closure can be characterized in that the height profile of its upper and lower edge of the cover relative to the base surface and also, for example, the distance of the lower edge of the cover from individual threads of a screw thread are measured.

As a result, any damage can be clearly assigned to a specific position on the bottle. In addition, the exact position of the label can be derived from the respective container data obtained, for example, in terms of its height position relative to the base surface as well as with respect to any inclinations. Also, the seat of the closure can be checked on the basis of the container data, namely whether a possible oblique seat is present, a suitable retaining ring is present, etc.

Various different features of the container must or should also be checked several times whilst being transported through the container handling system, in order, for example, to move the container from a work station into a correct position. It is also possible, up until a final check of the container, for different checking procedures to be carried out or carried out repeatedly. A modular configured inspection device with particularly or relatively easily replaceable checking stations is known.

With the known devices, however, the plurality of individual checking stations for carrying out the inspection procedures take up a large amount of structural space. The container stream must or should also be repeatedly stopped briefly at each individual checking station, or at least slowed down, as a result of which the run-through speed of the container is reduced.

OBJECT OR OBJECTS

An object of the present application is to provide a beverage bottle handling device for handling beverage bottles and similar containers in a beverage bottling or container filling plant.

The present application is therefore based on an object of providing a container handling system with a particularly or generally or relatively compact inspection device for inspecting a plurality of container features simultaneously or substantially simultaneously, which allows for a high run-through speed of the container.

SUMMARY

The present application solves the object by a container handling system disclosed in the present application. Further exemplifications of the present application are presented in the present application. In this situation, all or most or some of the features described are in principle the object of the present application, taken alone or in any desired combination.

The container handling system according to the present application comprises an inspection device for checking containers, in one possible exemplification drinks containers, and a container transport device for moving the containers into an inspection position of the inspection device, wherein the inspection device comprises at least two control modules, combined to one structural unit, from the group: control or detection module for checking a tamperproof securing element on a container closure, control or detection module for determining a filling quantity of the container, control or detection module for detecting the position of a closure logo on the container closure, control or detection module for determining the position of a code on the container, and/or control or detection module for detecting the position of a container label, wherein the container can be detected in the inspection position by at least two control or detection modules.

The combination of at least two control modules to form one structural unit allows for a particularly or generally or relatively compact configuration of the inspection device. As a result of this, the necessary and/or desired structural space for the inspection device can be perceptibly reduced, and the inspection device can be arranged particularly or generally or relatively easily in the container handling system, and in one possible exemplification into a container transport path, i.e. along a transport segment of the container through the container handling system.

In addition to this, the inspection device with at least two control modules allows for a particularly or generally or relatively wide range of application. For example, the structural unit can be arranged at a large number of different positions along the transport segment, and allows, on a particularly or generally or relatively short segment section of the transport segment, for a large number of checking possibilities of the container features.

The containers are, for example, drinks or beverage containers. These can be, in at least one possible exemplification of the present application, drinks bottles made of plastic or glass, which are, for example, at least partially transparent.

The term "container handling system" can be understood to mean an individual container handling station or a plurality of container handling stations, through which the containers run one after another. The container handling system is configured such as to guide the container through the container handling system, i.e. through or at the individual stations of the container handling system. For this purpose, the container handling system comprises in one possible exemplification a plurality of transporters for the linear or curved transport of the containers, or also transport stars for the transport of the containers on a circular track. The container transport device consequently transports the containers along a container transport path through the container handling system.

The term "inspection position" is understood to mean the position of the container in which a control module can inspect the container, i.e. for example can check, detect, or also determine a feature of the container. The term "features" in this connection is understood to mean in one possible exemplification markings introduced into or onto the container, embossings, codes, labels, or, inherently, characteristics of the container body, but also features such as, for example, the filling level of a container.

The term "control module" is understood in this connection to mean a device which inspects the actual state of one of the features of the container, and compares this with a target state, if appropriate with the aid of an evaluation unit or control unit.

In this situation, the control modules are configured in one possible exemplification for optical detection, i.e. for example for the imaging detection of a feature. Depending on the features which are to be detected, however, the control module can also comprise another sensor format for the inspection of a feature.

For a particularly or generally or relatively compact configuration of the structural element, and a particularly or generally or relatively versatile range of possible uses, provision is made, according to a further exemplification of the present application, for at least three, in one possible exemplification four, or for another possible exemplification at least five control modules to be grouped together to one structural unit.

For the inspection of the containers by the control modules, the container stream in one example is slowed down at least briefly in the region of the inspection position, or briefly stopped.

According to the present application, in the inspection position the container can be detected by at least two control modules, in at least one possible exemplification by at least three control modules, for at least one possible exemplification at least four control modules, and for still a further possible exemplification at least five control modules.

The inspection of the container by a plurality of control modules in one single inspection position is possible, since the run-through speed of the containers is scarcely reduced. In this situation, the inspection of the container can take place, for example, simultaneously or substantially simultaneously by several control modules. It is also possible, for example, for all or most or some of the individual control modules to carry out the inspection process on the container, one after another.

For the inspection the containers are usually moved past at the control modules. However, in order to configure the control modules grouped together to one structural unit in a particularly or generally or relatively compact manner, provision is made according to a further exemplification of the present application for the container transport device to comprise a container transport path leading through the inspection device, along which the container is transported through the inspection device; i.e. that the containers are guided through the inspection device, and therefore either guided through the control modules and/or along them.

As already mentioned, the control or detection modules are configured in at least one possible exemplification for the optical inspection of the containers; i.e. the control modules can in at least one possible exemplification produce an image of the container or of a container section with the feature which is to be inspected. In order to achieve a particularly or generally or relatively high precision of the control module at the inspection of the container feature, provision is made according to a further exemplification of the present application for the inspection device to comprise a lighting means, in at least one possible exemplification a transmitted light lighting means for the transmitted lighting of the container, a ring lighting, and/or a direct lighting arrangement for the direct lighting of the container.

The lighting means or arrangement can be arranged and configured in such a way that it provides adequate light for all or most or some of the control modules comprising the structural unit. In at least one possible exemplification of the present application, with the arrangement of different lighting means, such as transmitted lighting, ring lighting, or direct lighting, the individual lighting means can be configured such as to provide a possible light situation for one or more control modules. The lighting means can there be arranged separately from one another, and can be separately controlled. In at least one possible exemplification of the present application, they are activated briefly at the moment of the inspection procedure of the respective control module. In this situation it is also possible, for example, for different lighting means, such as, for example, the ring lighting and the direct lighting, to be activated simultaneously or substantially simultaneously at the inspection procedure of one or more control modules. In consequence, it is likewise possible for the lighting means to be actuated in such a way that individual lighting means are not activated during the inspection process of a control module, while other lighting means are activated.

In order to achieve a possibly good lighting of the container from its upper side, for example in order to improve a position detection of a closure logo on a container closure, a ring lighting is possible, arranged coaxially about a longitudinal axis of the container in the inspection position.

In this situation, the ring lighting is arranged in at least one possible exemplification in a plane above the container. The ring lighting therefore allows a uniform lighting of the container from all or most or some sides, or at least of an upper section of the container, such as, for example, a bottle neck and/or a container closure.

In order to light the container from one side in a possibly uniform manner, or, in at least one possible exemplification, a container section at which a label is arranged, for example, and from one side possibly well, the direct lighting exhibits for at least one possible exemplification two lighting bodies, arranged at a distance from one another on a first side of the container transport path.

The lighting bodies are in this situation arranged in such a way, for example, that they are arranged in the region of a label, and in at least one possible exemplification at an upper edge and at a lower edge of a label. In this situation, the lighting bodies extend in at least one possible exemplification transverse to the longitudinal axis of the container, such that it is essentially guaranteed and/or promoted that the container is fully lit at least from one side (for example a circumference of one hundred eighty degrees).

According to a further exemplification of the present application, provision is further made for the transmitted lighting to comprise a flat lighting body arranged on a second side of the container transport path.

In order to allow for a possibly good lighting of the container, for example for the detection of a transmitted light image (such as a shadow image) of the container or of a container section, the lighting body representing the transmitted lighting extends in at least one possible exemplification in the longitudinal axis direction and transverse to the longitudinal axial direction of the container. It can be configured, for example, as a rectangular lighting body.

As already mentioned heretofore, the inspection by the control modules takes place in one possible exemplification in an optical manner. In order, in addition, to allow for the inspection of the container by a plurality of control modules in one single inspection position, provision is made according to a further exemplification of the present application for at least one control module to comprise at least one camera and/or at least one beam deflection element for the optical inspection of the container.

The beam deflection elements allow in this case for the arrangement of the camera in an indirect position, i.e. in a position in which the feature which is to be detected by the camera does not lie in the direct detection range of the camera when the container is in the inspection position. Accordingly, depending on the position of the camera, it is also possible for a plurality of beam deflection elements pertaining to the camera to be arranged.

For example, with a control module for checking the tamperproof securing element which is configured for the detection of a one hundred eighty degree part region of the tamperproof securing element, up to five beam deflection elements can be arranged on one camera.

The beam deflection elements can, for example, be configured as flat mirrors. The beam deflection elements can also be structural bodies with a plurality of mirror surfaces, configured in at least one possible exemplification as triangular in cross-section. Beam deflection elements can also be configured as prisms, which deflect and/or bundle a light beam.

In order to provide a possibly compact configuration of the structural unit, provision is made according to a further exemplification of the present application for at least one camera to be arranged in an upper camera plane arranged above the transport device. As an alternative or supplement, in one possible exemplification at least one camera is arranged in a lower camera plane, parallel or substantially parallel to the upper camera plane but displaced in the direction onto the transport device.

In this connection, with the arrangement of a plurality of cameras, the term "plane" is understood to mean that the cameras of a plane exhibit to the greatest possible extent the same distance spacing from the transport plane; i.e. the perpendicular or substantially perpendicular height position of the cameras of a plane is at least as far as possible the same.

In order to configure the structural unit possibly compactly and to configure the operational possibilities of the structural unit for a possibly large number of features of the container, provision is made according to a further exemplification of the present application that: the control module for checking the tamperproof securing element comprises, in an inlet region of the container into the inspection device and/or in an outlet region of the container out of the inspection device, at least one camera and a beam deflection element, and/or the control module for determining the filling quantity of the container and/or the control module for determining the code position on the container and/or the control module for determining the position of the container label on the first side of the transport path comprises a camera and a beam deflection element, and/or the control module for determining the position of the closure logo on the container closure comprises a camera arranged perpendicularly or substantially perpendicularly above the inspection position.

The above-discussed exemplifications of the present invention will be described further herein below. When the word "invention" or "exemplification of the invention" is used in this specification, the word "invention" or "exemplification of the invention" includes "inventions" or "exemplifications of the invention", that is the plural of "invention" or "exemplification of the invention". By stating "invention" or "exemplification of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

DESCRIPTION OF EXEMPLIFICATION OR EXEMPLIFICATIONS

Figure 1:
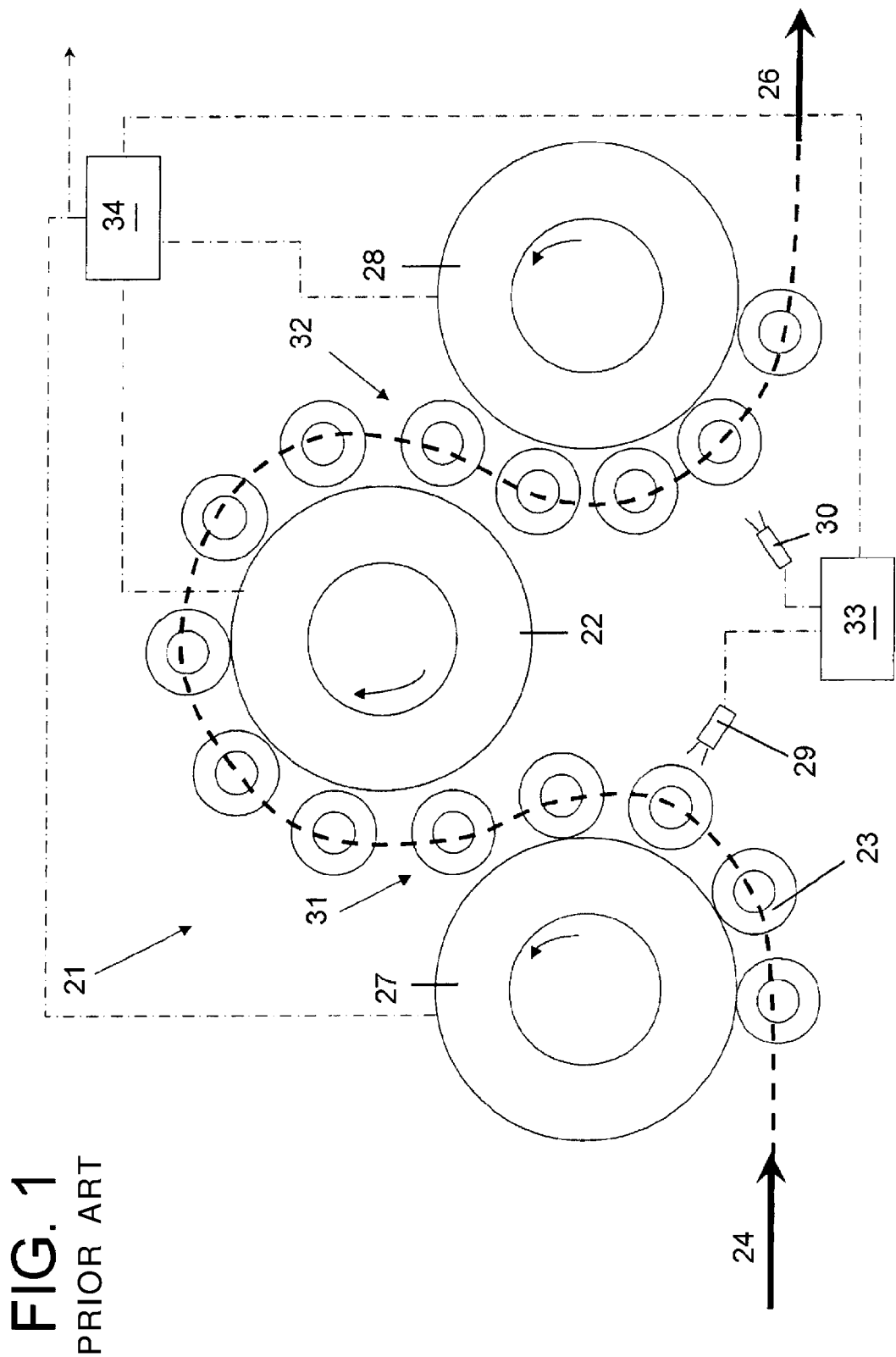
FIG. 1 shows an example of a beverage bottle handling machine for handling beverage bottles and similar containers.

FIG. 1 shows an example of a beverage bottle handling machine for handling beverage bottles and similar containers, as disclosed in DE102008034744. The handling machine in the example shown is a labeling machine 21, which has a labeling carousel 22, at which labeling can be performed.

The containers 23 to be labeled are supplied to the labeling carousel 22 at an inlet side (arrow 24). The labeled containers 23 are discharged from the labeling carousel 22 on a discharge side (arrow 26).

At the inlet side (arrow 24) and at the outlet side (arrow 26), an inspection carousel 27 or 28 is respectively arranged in the illustrated embodiment. It is entirely within the meaning of the present application to omit the inspection carousel 27 and only have an inspection carousel 28 on the outlet side. The inspection carousels 27 and 28 are executed on the one hand as inlet carousel 27 and the other as a outlet carousel 28. The inlet carousel 27 is arranged on the inlet side (arrow 24), wherein the outlet carousel 28 is arranged on the outlet side and cooperates directly with the labeling carousel 22.

The inlet carousel 27, preferably the labeling carousel 22, and the outlet carousel 28 are preferably designed to be identical. In the illustrated embodiment, the containers 23 are bottles, which are provided to the labeling carousel 22 in the filled state with a closure or closed with a lid. The containers 23 and the exemplary bottles can be made of a transparent or translucent material, for example, of glass or of a translucent plastic, for example, PET.

The inlet carousel 27 and the outlet carousel 28 each have inspection devices 29 and 30, which are shown in principle in the manner of a camera. For the sake of clarity, only one inspection device 29 and 30 is respectively arranged on the respective carousel 27 or 28. Of course, it is within the meaning of the present application that at least the outlet carousel 28 has a plurality of inspection devices 30, which perform the same or different inspection tasks.

For example, the inlet carousel 27 may include a foreign object inspection device. With the foreign object inspection, the containers can be inspected for unwanted objects inside them.

The outlet carousel 28 can, for example, have inspection devices relating to a fill level control, and/or have a label equipment control, to name just a few examples. The container 23 can be adjusted to a desired orientation of the applied labels, for example, be inspected based on embossing. At the same time, incorrectly attached or damaged labels (e.g. kinks, cracks) are detected.

The containers 23 are fed to the inlet carousel 27, which first passes the containers 23 past the relevant inspection device 29, and transfers them to the labeling carousel 22. A transfer area is conceivable, for example, at 31. For positionally stable transport in the labeling carousel 22, gripping devices, for example, so-called tulip grips, are provided which grip at the mouth region of the container 23. Alternatively the container 23 is mounted on a respective associated turntable. It is conceivable that on the labeling carousel 22 an inspection device for aligning the container is arranged in a desired position for labeling, which can cause a twisting of the container from an actual position to the desired position by driving the separately controllable turntable. Of course, such measures can also be performed in the area of inlet carousels 27, wherein the container 23 can be transferred in the desired position to the labeling carousel 22.

The inlet carousel 27 acts directly with the labeling carousel 22 together. The containers 23 are guided past the labeling units (not shown) in the desired position, and transferred at an exemplary transfer area at 32 to the outlet carousel 28, which also has corresponding gripping devices. At least at the outlet carousel 28, a clamping mechanism may be arranged as a gripping device, which guides the container 23 stable in position and aligned with the respective inspection devices 30. The containers 23 are guided past the inspection device or devices 30, and then discharged from the labeling machine 21.

The respective inspection devices 29 and 30 and also the inspection device for aligning the containers in a desired position for labeling are part of a monitoring system with a control unit 33, in which the images or image data supplied by the respective camera are evaluated, with respect to the individual (same or different) inspection tasks. The processing of the images or image data supplied by the camera takes place, for example, by comparison with setpoint data stored in the control unit 33. In this respect, the control unit 33 may also be referred to as image processing and control unit 33. The control unit 33 is, for example, a computer or a computer-aided unit with corresponding inputs for analog or digital data supplied by the respective camera. Next, the control unit 33 is connected with the individual components (e.g., container orientation, labeling) of the labeling machine are connected to correct corresponding deviations of the actual data of desired data, so that the labeling machine 21 is quasi self-controlled or self regulates in relation to the bottles. In the illustrated example, the control unit 33 is connected to a central further control unit 34, which controls and further processes the data of the control unit 33 with respect to the entire system.

For example, if the inspection device 29 detects that a container has foreign matter inside it, that container will not be labeled. If the inspection device 29 detects, for example, that the applied label is arranged incorrectly and/or damaged, the container in question is sorted out at a suitable location.

Figure 2:
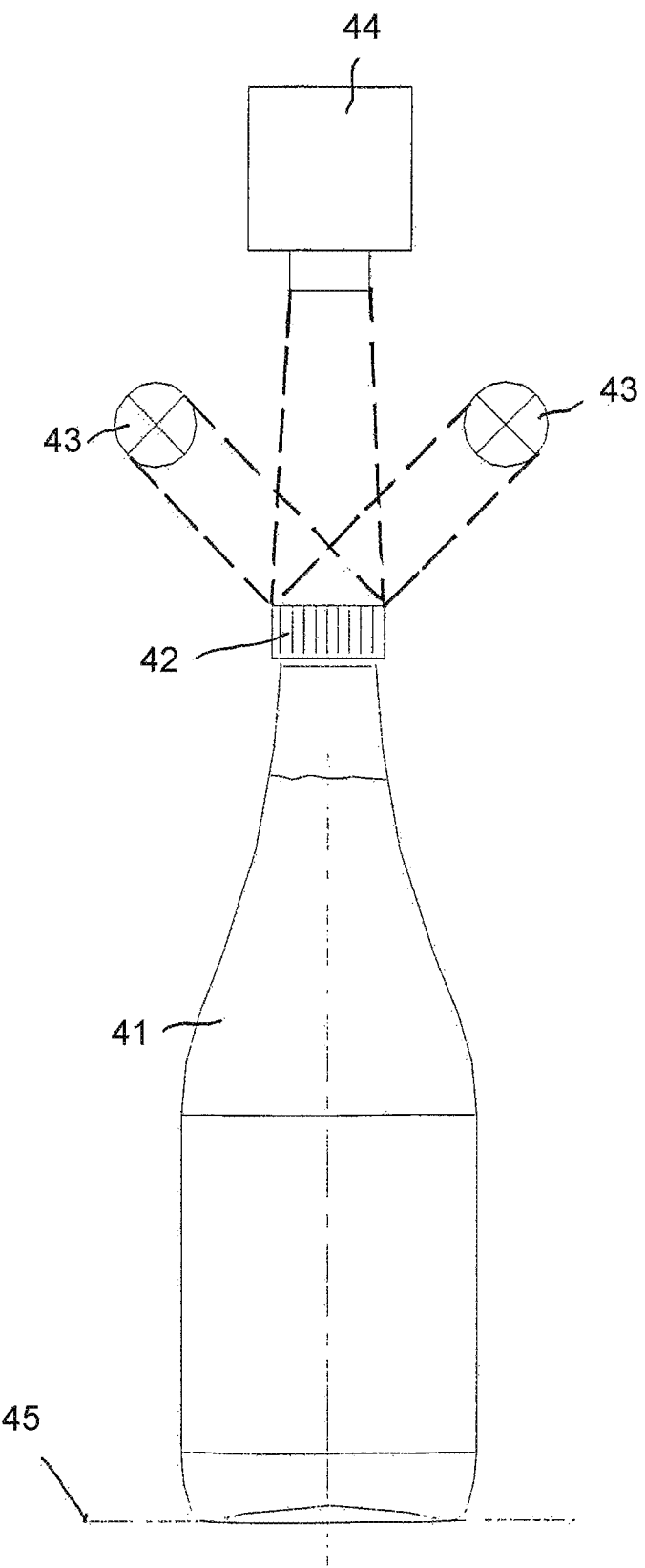
FIG. 2 shows an example of a beverage bottle or similar container with a container closure thereon.

FIG. 2 shows an example of a beverage bottle or similar container with a container closure thereon, as disclosed in published international patent application WO03/024859. Over a continuously movable conveyor belt 45, there is a CCD camera 44 directed downwards perpendicular to the conveyor belt with an image memory and a device (image evaluation electronics) for the evaluation (analysis) of recorded images, and for generating a signal for displaying and/or discharging bottles that do not conform to a specified standard.

Concentric with the optical axis of the camera, an annular light source 43 is arranged, which may for example comprise a plurality of LEDs positioned on a downwardly open and outwardly flared conical surface (inner surface). The camera and bottle movement are suitably synchronized, pulsed, driven LEDs.

The height and geometry of the light source 43 is designed so that the shutter 42 on the mouth of a bottle 41, currently located with its vertical center axis 41 coaxial with the optical axis under the camera 44, is fully obliquely illuminated from above and outside, in particular its outer edge that reflects incident light up to the camera 44.

As soon as the continuously moving bottle 41 is in the shown, coaxial position under the camera 44, this receives with the shutter 42 simultaneous illumination by the light source 43, that is, from the top of the shutter, is taken and stored in the image memory of the image evaluation of the camera.

Figure 3:
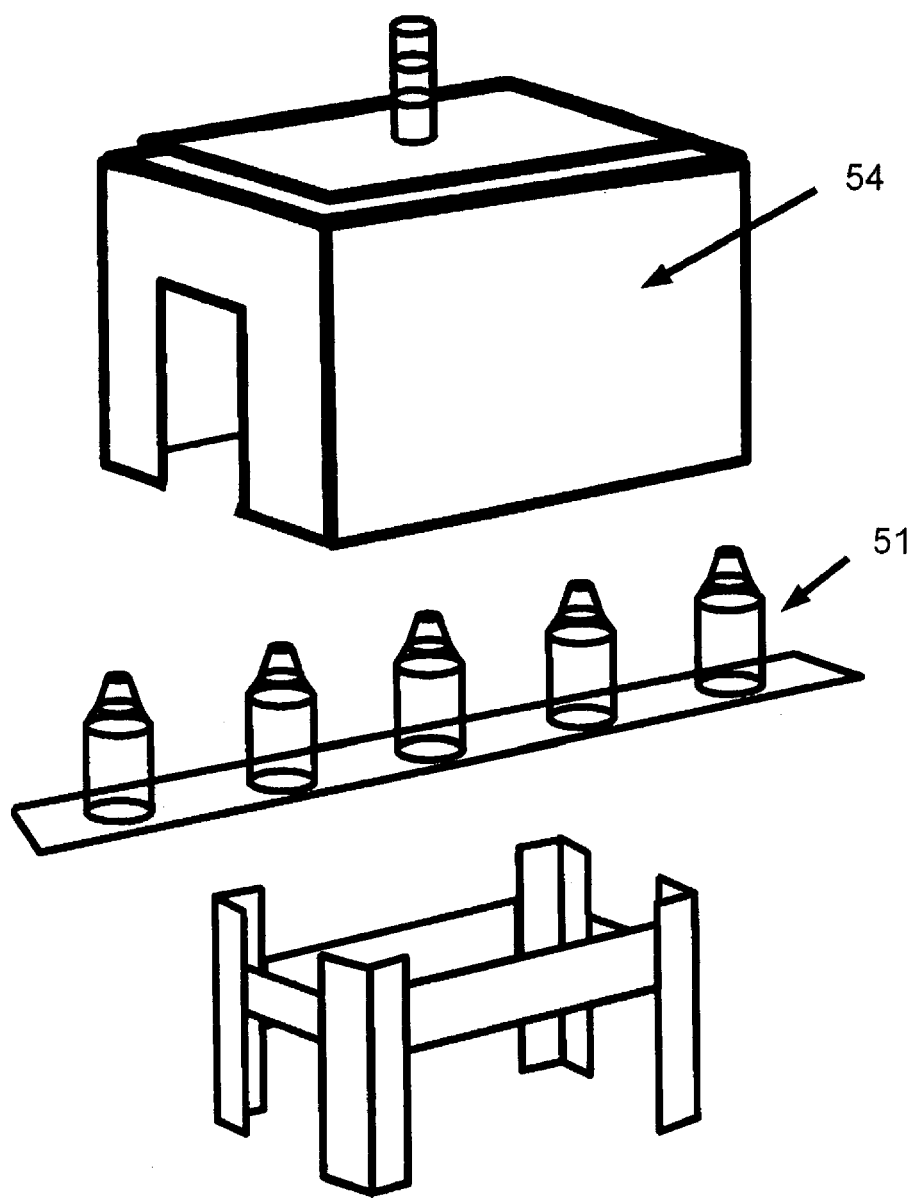
FIG. 3 shows an example of a beverage bottle handling machine.

FIG. 3 shows an example of a beverage bottle handling machine, as disclosed in published European patent EP1715328. Such inspection machines, but also those of rotary construction, show essentially the following structure: the containers 51 are standing upright on a transport conveyor, for example, a transport chain. For inspection of the container, an inspection station is formed, which forms part of the transport path or encloses a part of the transport path. For this purpose, it is known to form an enclosure which, as part of the inspection station, encloses the transport path in the inspection area as completely as possible and in a light-tight manner, so that as a rule only the container inlet and outlet are not closed by the wall of the enclosure 54.

Figure 4:
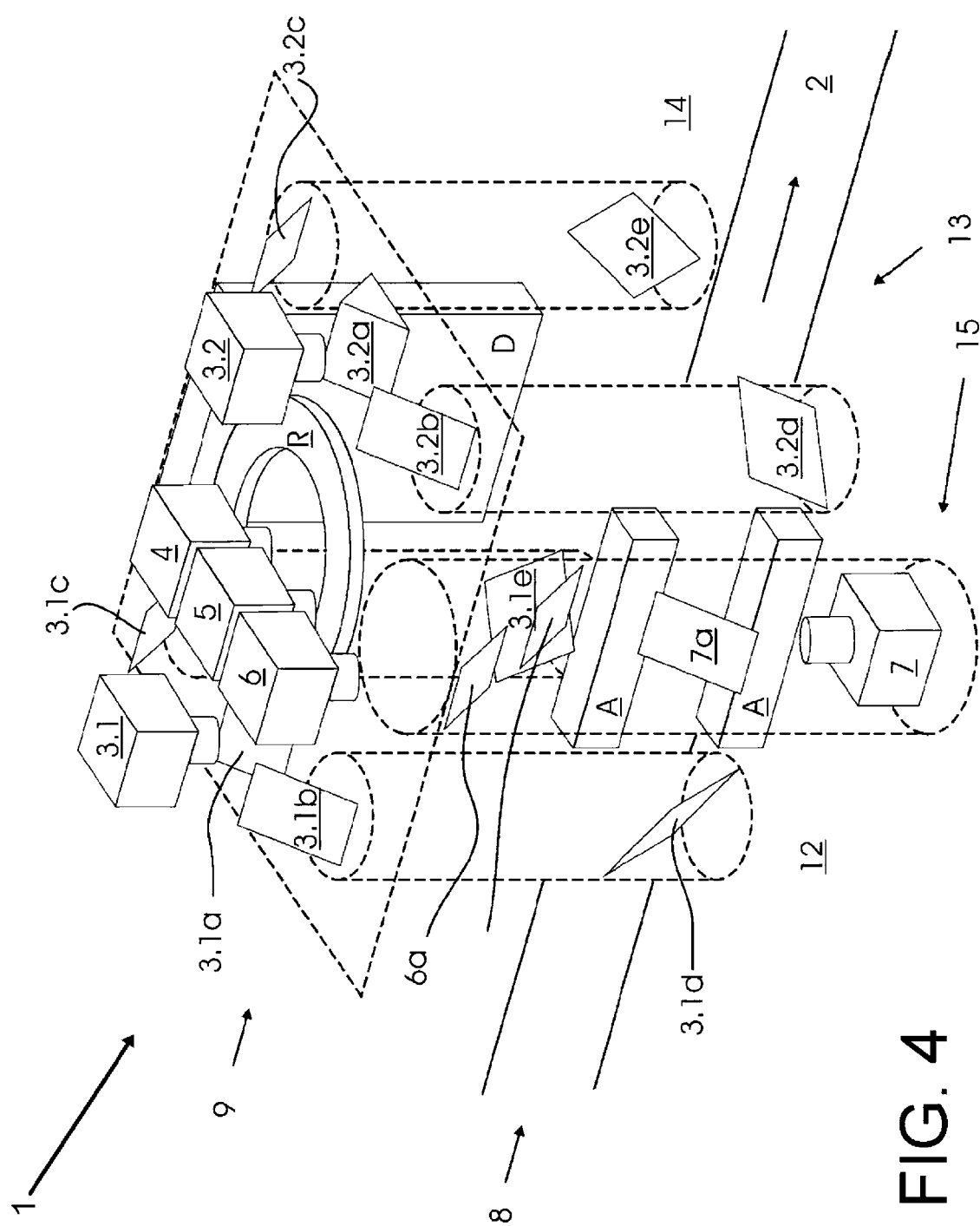
FIG. 4 shows schematically, in a perspective representation, an inspection device arranged at a container transport system.

FIG. 4 shows an inspection device 1, which is arranged at a container transport device 2, belonging to a container handling system (not represented here). The container transport device 2 guides the containers 11 (see FIG. 5), in this case, in at least one possible exemplification, transparent bottles, along a transport segment through the container handling system. The transport direction is represented by an arrow.

The inspection device 1 comprises five different control modules, grouped together to form a structural unit. A first control module is configured for the checking of a quality securing element at a container closure (not represented here); i.e. the control module can inspect a securing structure such as a ring arranged at a container closure, which it is intended should be damaged at the opening of the container closure.

In order to check the securing ring, which runs completely around the bottle neck, from all sides (total side inspection) or most sides or some sides, the first control module comprises two cameras 3.1, 3.2 for the image detection. The cameras 3.1, 3.2 are arranged spaced at a distance from one another, wherein the first camera 3.1 is arranged in the region of a container inlet 8 and perpendicular or substantially perpendicular above the container transport device 2 in a region of an upper camera plane 9. The second camera 3.2 of the first control module is likewise arranged in a region of the upper camera plane 9 and perpendicular or substantially perpendicular above the container transport device 2, but in the region of a container outlet 13 from the inspection device 1.

Belonging to each camera 3.1, 3.2 are five beam deflection elements 3.1*a*-3.1*e*, 3.2*a*-3.2*e*. Arranged perpendicularly or substantially perpendicularly beneath each camera 3.1, 3.2 is in each case a triangular beam deflection element 3.1*a*, 3.2*a*, with two mirror surfaces. Each of the mirror surfaces is in turn aligned with a further mirror surface of an upper beam deflection element 3.1*b*, 3.1*d*, 3.2*b*, 3.2*d*.

The mirror surfaces of the upper beam deflection elements 3.1*b*, 3.1*d*, 3.2*b*, 3.2*d* are in turn aligned in each case to a lower beam deflection element 3.1*d*, 3.1*e*, 3.2*d*, 3.2*e*, configured as mirrors. As a consequence, the upper beam deflection elements 3.1*a*-3.1*c*, 3.2*a*-3.2*c* are arranged in an upper beam deflection plane arranged parallel or substantially parallel to the transport device, and the lower beam deflection elements 3.1*d*, 3.1*e*, 3.2*d*, 3.2*e* are arranged in a lower beam deflection plane.

The lower beam deflection elements 3.1*d*, 3.1*e*, 3.2*d*, 3.2*e* are additionally aligned onto an inspection position P (see FIG. 5), such that a container closure of a container (11) located in the inspection position P can be checked by way of the beam deflection elements 3.1*a*-3.2*e*.

A second control module likewise comprises a camera 4 arranged in the region of the upper camera plane 9 for image detection, which is configured for the location detection of a logo on a container closure upper side, and is arranged perpendicularly or substantially perpendicularly above the inspection position P, i.e. in an extension of the longitudinal axis of the container 11. The second control module therefore likewise detects the location of the logo, as soon as the container 11 is in the inspection position P.

A third control module comprises, like the first and second control modules, a camera 5 arranged perpendicularly or substantially perpendicuarly above the container transport device 2 and in the upper camera plane 9, which is configured for determining the filling quantity in the container 11. The camera 5 and the beam deflection element 5*a* allocated to it are arranged in the region of a first side 12 of the transport segment of the container transport device 2.

A fourth control module likewise comprises a camera 6, arranged perpendicularly or substantially perpendicularly above the container transport device 2 and in the upper camera plane 9, which is configured for the determination of a code position. Corresponding to the camera 5 for determining the filling quantity, the camera 6 of the fourth control module, and a beam deflection element 6*a* allocated to it, are also arranged in the region of the first side 12 of the transport segment of the container transport device 2.

The fifth control module is configured for the location of the position of a label on the container 11, and comprises a camera 7 for image detection, which, together with a beam deflection element 7*a* allocated to it, is likewise arranged in the region of the first side 12 of the transport segment. The camera 7 of the fifth control module, however, is arranged in a lower camera plane 15, displaced perpendicularly or substantially perpendicularly to the upper camera plane 9 in the direction of the container transport device 2.

In order to obtain a possibly good lighting of the container 11 in the inspection position during the inspection, three different lighting means are arranged.

On the one hand, arranged adjacent to and beneath the upper camera plane 9 is a ring lighting R, which extends coaxially about a perpendicular or substantially perpendicular longitudinal axis of the inspection position P. The ring lighting R lights up in at least one possible exemplification the closure logo at the container closure.

The cameras 3.1, 3.2, 4, 5, 6, & 7 can be connected to a computer arrangement which compares the images from the cameras to acceptable images stored in the computer arrangement and discerns whether the images received are acceptable. If not, the computer generates signals to remove the unacceptable containers from the production line and/or feed signals back to the container filling plant to make connections to the appropriate parts of the container filling plant.

Figure 5:
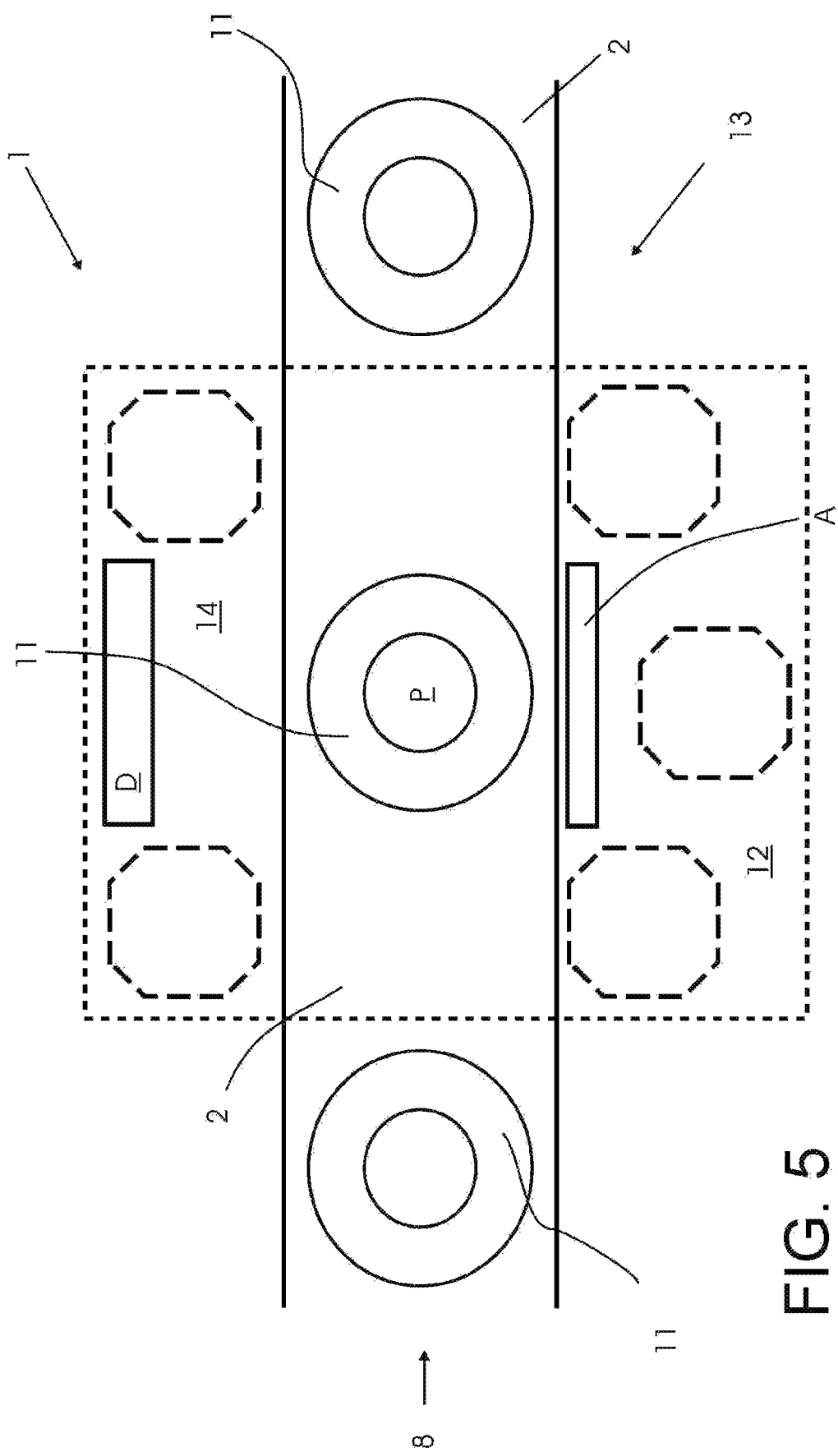
FIG. 5 schematically, in a cross-section, the inspection device from FIG. 4.

As shown in FIG. 5, arranged on the second side 14 of the transport segment of the container transport device 2 is a flat (rectangular) transmitted light lighting body D. The transmitted light lighting body D serves in at least one possible exemplification for the transmitted lighting of the (transparent) container 11 (bottle), for example at the checking of the tamperproof securing element, by means of the first control module or at the detection of the filling quantity of the container 11 by means of the second control module.

For possibly good lighting of the container 11, for example, a lens (not represented here) can be arranged at the transmitted light lighting body D, in at least one possible exemplification a film lens, such as a Fresnel's film lens disposed in lighting body D, which directs the light beams of the transmitted light lighting body D into a specific spatial direction, for example in a spatial direction perpendicular or substantially perpendicular to the surface of the transmitted light lighting body D.

Figure 5A:
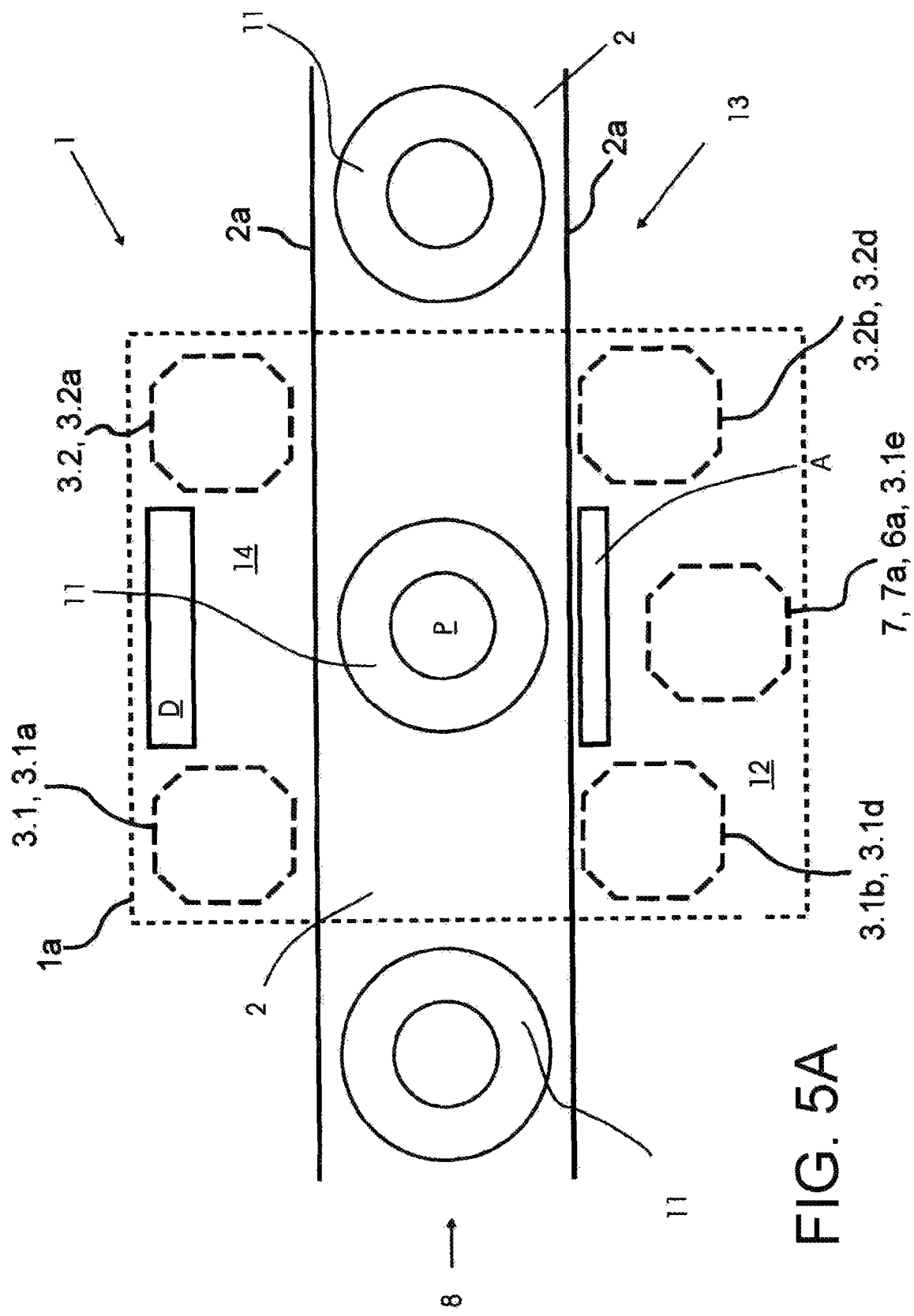
FIG. 5A shows the details of FIG. 5 with additions.

As can be seen in FIG. 5A, the bottle 11 is surrounded by the detector module components 3.1, 3.2, 3.1a-3.2e, 4, 4a, 5, 5a, 6, and 6a among other components of the inspection device 1. For example, the bottle 11 may typically be a twelve-ounce or thirty-three-centiliter bottle which has a diameter of about two inches (twenty-five millimeters). As can be seen from FIG. 5A, the distance from 3.1, 3.1a is about the same as or a little less than the diameter of the bottle 11. Other bottles such as 10 oz., 8 oz., 16 oz., 20 oz., 1 liter, 600 mL, 1½ liter, etc, usually used in commerce, have somewhat smaller and larger diameters which could require different spacing. The direct light A is spaced at about ¼ of the diameter of the bottle 11 and the transmitted light of A at about the diameter of the bottle 11: other components are also spaced closely around or above the bottle 11.

The components of the inspection device 1 are disposed immediately adjacent the container transport device, such as a transport belt, 8 and typically just few millimeters from the edges 2a thereof.

In addition, a direct lighting arrangement A is arranged, which is well-suited in at least one possible exemplification for the better lighting of the side of the container 11 oriented towards the first side 12 of the transport segment. This can therefore be used, for example, for determining the position of the container label or also for determining the code position. The direct lighting arrangement A is arranged on the first side of the transport segment, and comprises two lighting bodies, spaced perpendicular or transverse or substantially perpendicular at a distance from one another, which extend transverse to the longitudinal axis of the container. The direct lighting arrangement A is arranged parallel or substantially parallel to the transmitted lighting D.

In operation, a container stream of a plurality of containers 11, in this case filled transparent drinks bottles, is moved by means of the transport device 2 into the inspection device 1. The containers 11 were aligned before being moved in, such that the labels on the containers 11 point in the direction of the first side 12 of the transport segment. As an alternative, for example, a further control module belonging to the structural unit can be provided for detecting the position of the container 11 and for positioning the container 11.

As soon as a container 11 is present in the inspection position P, the control modules are activated in rapid sequence one after another. Simultaneously or substantially simultaneously with the control modules, the respective lighting means D, A, R are activated, in order to attain a possibly good lighting of the container 11 at the time of the inspection.

For example, at the activation of the camera 3.1, 3.2 for detecting the tamperproof security element, the transmitted lighting body D and, if appropriate, additionally the ring lighting R are activated. At the detection of the position of the closure logo, for example, the ring lighting R is activated, while at the activation of the control module for determining the filling quantity, for example, the transmitted lighting body D is activated. Finally, for example, with the activation of the control modules for determining a code position on the container 11 or for determining the position the location of the container label, the direct lighting A is activated.

As an alternative to this, the lighting means for the control modules can also be switched in another way, inasmuch as this allows for better lighting of the container 11 to be achieved at the inspection by the respective control module. It is also possible, for example, for individual or a plurality of lighting means to be activated during the inspection of a control module or a plurality of control modules.

The sequence of the activation of the control modules and the lighting means A, D, R pertaining to them can be freely arranged. Accordingly, therefore, it is also possible for one, two, three, or four control modules to be activated simultaneously or substantially simultaneously with one another. One factor to be taken into account in this situation is the fact that, for a possibly good quality of image detection, control modules/lighting units which function opposed to one another should generally not be activated simultaneously or substantially simultaneously but one after another. Accordingly, for example, a control module which is assigned to a transmitted light arrangement is, as far as possible, not activates as soon as the direct lighting is activates.

Once all or most or some of the necessary and/or desired control modules have been activated, the container 11 is transported by means of the transport device 2 out of the inspection device 1 again.

In principle, the lighting units are configured, for example, to produce white light. This relates in at least one possible exemplification to the transmitted lighting element D. As an alternative, for example, it is also possible for one or more of the lighting elements A, R, D to be configured so as to produce another type of light, such as an infrared light.

The present application relates to a container handling system having an inspection device 1 for checking containers 11, in one possible exemplification drink containers, and a container transport device 2 for moving the containers into an inspection position P of the inspection device 1. In order to provide a container handling system having a possibly compact inspection device designed to check a plurality of container features, provision is made for the inspection device to have at least two control modules from the following group which are combined to form a structural unit:—control module for checking a tamperproof securing element on a container closure,—control module for determining a filling quantity of the container,—control module for detecting the position of a closure logo on the container closure,—control module for determining the position of a code on the container and/or—control module for detecting the position of a container label.

One feature or aspect of an exemplification is believed at the time of the filing of this patent application to possibly reside broadly in a container handling system comprising an inspection device 1 for checking containers 11, in one possible exemplification drinks containers, and a container transport device 2 for moving the containers 11 into an inspection position P of the inspection device 1, wherein the inspection device 1 comprises at least two control modules combined to form one structural unit, selected from the group: control module for checking a tamperproof security element on a container closure, control module for determining a filling quantity of the container 11, control module for determining the position of a closure logo on the container closure, control module for determining a code position on the container 11 and/or control module for determining the position of a container label, wherein the container 11 in the inspection position P can be detected by at least two control modules.

Another feature or aspect of an exemplification is believed at the time of the filing of this patent application to possibly reside broadly in the container handling system, wherein at least three, in one possible exemplification at least four, and in a further possible exemplification at least five control modules are combined to form a structural unit.

Yet another feature or aspect of an exemplification is believed at the time of the filing of this patent application to possibly reside broadly in the container handling system, wherein the container 11 in the inspection position P can be detected by at least three control modules, in at least one possible exemplification by four control modules, and in a further possible exemplification by at least five control modules.

Still another feature or aspect of an exemplification is believed at the time of the filing of this patent application to possibly reside broadly in the container handling system, wherein the container transport device 2 comprises a container transport segment leading through the inspection device 1, along which the containers 11 can be transported through the inspection device 1.

A further feature or aspect of an exemplification is believed at the time of the filing of this patent application to possibly reside broadly in the container handling system, wherein the inspection device 1 comprises a lighting means, in one possible exemplification a transmitted light arrangement D for transmitted lighting of the container 11, a ring lighting arrangement R, and/or a direct lighting arrangement A for lighting the container 11.

Another feature or aspect of an exemplification is believed at the time of the filing of this patent application to possibly reside broadly in the container handling system, wherein the ring lighting arrangement is arranged coaxially to a longitudinal axis of the container 11 in the inspection position P.

Yet another feature or aspect of an exemplification is believed at the time of the filing of this patent application to possibly reside broadly in the container handling system, wherein the direct lighting arrangement A comprises two lighting bodies arranged at a distance spacing from one another on a first side 12 of the container transport segment.

Still another feature or aspect of an exemplification is believed at the time of the filing of this patent application to possibly reside broadly in the container handling system, wherein the transmitted lighting arrangement D comprises a flat lighting body arranged on a second side 14 of the container transport segment, opposite the first side 12.

A further feature or aspect of an exemplification is believed at the time of the filing of this patent application to possibly reside broadly in the container handling system, wherein at least one control module comprises at least one camera 3.1, 3.2, 4, 5, 6, 7 and/or at least one beam deflection element 3.1a-3.2a, 5a, 6a, 7a for optical checking of the container 11.

Another feature or aspect of an exemplification is believed at the time of the filing of this patent application to possibly reside broadly in the container handling system, wherein at least one camera 3.1, 3.2, 4, 5, 6 is arranged in an upper camera plane 9 arranged above the container transport device 2.

Yet another feature or aspect of an exemplification is believed at the time of the filing of this patent application to possibly reside broadly in the container handling system, wherein at least one camera 7 is arranged in a lower camera plane 15, arranged parallel or substantially parallel to the upper camera plane 9 and displaced in the direction onto the container transport device 2.

Still another feature or aspect of an exemplification is believed at the time of the filing of this patent application to possibly reside broadly in the container handling system, wherein the control module for checking the tamperproof security element in an inlet region of the container 11 into the inspection device 1 and/or in an outlet region of the container 1 out of the inspection device 1 comprises at least one camera 3.1, 3.2, 4, 5, 6, 7 and a beam deflection element 3.1a-3.2e, 5a, 6a, 7a, and/or the control module for determining the filling quantity of the container 11 and/or the control module for determining the code position on the container 11 and/or the control module for determining the position of the container label 3.1, 3.2, 4, 5, 6, 7 and a beam deflection element 3.1a-3.2e, 5a, 6a, 7a, and/or the control module for determining the position of the closure logo on the container closure comprises a camera 3.1, 3.2, 4, 5, 6, 7 arranged perpendicularly or substantially perpendicularly above the inspection position P.

One feature or aspect of an exemplification is believed at the time of the filing of this patent application to possibly reside broadly in a container handling system comprising: an inspection device to check containers, such as beverage containers; and a container transport device for moving the containers into an inspection position of the inspection device; said inspection device comprising a framework or housing or other structure to hold modules of the inspection device about a container which inspection device comprises at least two detection modules disposed about said framework or housing or other structure and form a single structural unit about a container; said detection modules selected from a group comprising: A) a detection module configured to check a tamperproof security element on a container closure configured to check said module; B) a detection module configured to check a filling quantity of a container; C) a detection module configured to check the position of a closure logo on a container closure; D) a detection module configured to check a code position on a container; and E) a detection module configured to check a position of a container label; wherein a container in the inspection position is detectable by at least two of said detection modules.

Another feature or aspect of an exemplification is believed at the time of the filing of this patent application to possibly reside broadly in the container handling system according to claim 1, wherein said at least two modules comprising one of: a) at least three modules; b) at least four modules; and c) at least five control modules; which modules are combined in said framework or housing or other structural unit.

Another feature or aspect of an exemplification is believed at the time of the filing of this patent application to possibly reside broadly in the container handling system, wherein said system is configured to detect a container in the inspection position that is detectable by at least said three modules.

Yet another feature or aspect of an exemplification is believed at the time of the filing of this patent application to possibly reside broadly in the container handling system, wherein said system is configured to detect a container with said at least two modules comprising four detection modules.

Still another feature or aspect of an exemplification is believed at the time of the filing of this patent application to possibly reside broadly in the container handling system, wherein said system is configured to detect a container with at least said five detection modules.

A further feature or aspect of an exemplification is believed at the time of the filing of this patent application to possibly reside broadly in the container handling system, wherein said container transport device comprises a container transport segment leading through said inspection device, along which containers are transportable through said inspection device.

Another feature or aspect of an exemplification is believed at the time of the filing of this patent application to possibly reside broadly in the container handling system, wherein the inspection device comprises a lighting arrangement comprising at least one of: a) a transmitted light arrangement disposed to transmit lighting to a container; b) a ring lighting arrangement disposed coaxially to a longitudinal axis of a container in an inspection position; and c) a direct lighting arrangement to light a container; each of a), b) and c) are disposed to transmit light to a container.

Yet another feature or aspect of an exemplification is believed at the time of the filing of this patent application to possibly reside broadly in the container handling system, wherein the direct lighting arrangement comprises one of a) and b): a) two lighting bodies arranged at a distance spacing from one another on a first side of the container transport device; and b) a flat lighting body disposed on a second side of the container transport device, opposite said first side.

Still another feature or aspect of an exemplification is believed at the time of the filing of this patent application to possibly reside broadly in the container handling system, wherein at least one of said modules comprises at least one of: a) at least one camera; and b) at least one beam deflection element configured to optically check a container.

A further feature or aspect of an exemplification is believed at the time of the filing of this patent application to possibly reside broadly in the container handling system, wherein said at least one camera is disposed in an upper camera plane disposed above said container transport device.

Another feature or aspect of an exemplification is believed at the time of the filing of this patent application to possibly reside broadly in the container handling system, wherein said at least one camera is disposed in a lower camera plane, being disposed parallel to an upper camera plane and displaced in a direction onto the container transport device.

Yet another feature or aspect of an exemplification is believed at the time of the filing of this patent application to possibly reside broadly in the container handling system, including at least one of I, II, and III: I) said detection module for checking the tamperproof security element is disposed at one of: a) in an inlet region of a container in said inspection device or in an outlet region of said container inspection device; b) at said inspection device which comprises at least one of the cameras and a beam deflection element; and II) at least one of the detection modules is configured to determine: c) the filling quantity of a container; d) a code position on a container; e) a position of the container label; and f) a position of the closure logo on the container closure comprises a camera being disposed perpendicularly or directly above an inspection position; and III) a beam deflection element.

Still another feature or aspect of an exemplification is believed at the time of the filing of this patent application to possibly reside broadly in the container handling system, wherein said beam deflection element comprises a film lens.

A further feature or aspect of an exemplification is believed at the time of the filing of this patent application to possibly reside broadly in the container handling system, wherein said beam deflection element comprises a film Fresnel's lens.

One feature or aspect of an exemplification is believed at the time of the filing of this patent application to possibly reside broadly in a method of inspecting containers by operating a container handling system, said system comprising: an inspection device to check containers, such as beverage containers; and a container transport device for moving the containers into an inspection position of the inspection device; said inspection device comprising a framework or housing or other structure to hold modules of the inspection device about a container which inspection device comprises at least two detection modules disposed about said framework or housing or other structure and form a single structural unit about a container; said detection modules selected from a group comprising: A) a detection module configured to check a tamperproof security element on a container closure configured to check said module; B) a detection module configured to check a filling quantity of a container; C) a detection module configured to check the position of a closure logo on a container closure; D) a detection module configured to check a code position on a container; and E) a detection module configured to check a position of a container label; wherein a container in the inspection position is detectable by at least two of said detection modules; said method comprising the step of detecting outputs of said at least two detection modules.

Another feature or aspect of an exemplification is believed at the time of the filing of this patent application to possibly reside broadly in the method, wherein said detecting with at least two modules comprising one of: a) detecting with at least three modules, b) detecting with at least four modules, and c) detecting with at least five modules; which modules are combined in said framework or housing or other structural unit.

Yet another feature or aspect of an exemplification is believed at the time of the filing of this patent application to possibly reside broadly in the method, wherein said system is configured to detect a container in the inspection position and detecting with at least said three detection modules.

Still another feature or aspect of an exemplification is believed at the time of the filing of this patent application to possibly reside broadly in the method, wherein said system is configured to detect and detects said at least two detection modules comprising four detection modules.

A further feature or aspect of an exemplification is believed at the time of the filing of this patent application to possibly reside broadly in the method, wherein said inspection device is lighting at least one of: a) said transmitted light arrangement transmitting light to a container; b) said ring lighting arrangement transmitting light to a container; and c) said direct lighting arrangement transmitting light to a container.

Another feature or aspect of an exemplification is believed at the time of the filing of this patent application to possibly reside broadly in the method, including a film Fresnel's lens directing two light beams transverse to one another.

The components disclosed in the patents, patent applications, patent publications, and other documents disclosed or incorporated by reference herein, may possibly be used in possible exemplifications of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one exemplification in the application, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various exemplifications may be used with at least one exemplification or all of the exemplifications, if more than one exemplification is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications, patent publications, and other documents cited herein, and in the Declaration attached hereto, are hereby incorporated by reference as if set forth in their entirety herein except for the exceptions indicated herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, patent applications, patent publications, and other documents which are included in this application and which are referred to in paragraphs which state "Some examples of . . . which may possibly be used in at least one possible exemplification of the present application . . . " may possibly not be used or useable in any one or more exemplifications of the application.

The sentence immediately above relates to patents, patent applications, patent publications, and other documents either incorporated by reference or not incorporated by reference.

The following patent is hereby incorporated by reference as if set forth in its entirety herein except for the exceptions indicated herein, as follows: DE 10 2010 043 035 A1, having the English translation of the German title "Front module for a motor vehicle", published on May 3, 2012.

The following patents, patent applications, patent publications, and other documents, except for the exceptions indicated herein, are hereby incorporated by reference as if set forth in their entirety herein except for the exceptions indicated herein, as follows: DE 10 2010 043 635 A, having the English translation of the German title "Container inspecting apparatus", published on May 10, 2012; WO 2008/104273, having the title "METHOD AND INSPECTION DEVICE FOR EXAMINING CONTAINERS", published on Sep. 4, 2008; EP 1 715 328 A1, having the title "Inspection apparatus for inspecting sealed containers", published on Oct. 25, 2006; WO 03/024859, having the title "METHOD FOR INSPECTING CLOSURES ON CONTAINERS", published on Mar. 27, 2003; DE 10 2008 034 744 A1, having the English translation of the German title "Labeling machine, has labeling container led out from labeling carrousel at output side, inspection carrousel arranged at output side of labeling carrousel, and inspection devices utilized for same or different inspection tasks", published on Jan. 28, 2010; DE 10 2008 062 385 A1, having the German title "Verfahren sowie Inspektionsvorrichtung zum Überprüfen von Behältern", published on Jul. 8, 2010; and the article entitled "VISIONSYSTEM AUTOMATISIERT DAS ABFUELLEN VON GETRAENKEN" by author J. Lamprecht, published in Elektrotechnik fuer die Automatisierung, 19981105 Vogel Business Media GmbH & Co.KG, Vol: 80, Nr: 11, Page(s): 146,149; Federal Republic of Germany Patent Application No. 10 2014 102 119.4, filed on Feb. 25, 2014; International Application No. PCT/EP2015/053547, filed on Feb. 19, 2015, having WIPO Publication No. WO 2015/128245.

All of the references and documents cited in any of the patents, patent applications, patent publications, and other documents cited herein, except for the exceptions indicated herein, are hereby incorporated by reference as if set forth in their entirety herein except for the exceptions indicated herein. All of the patents, patent applications, patent publications, and other documents cited herein, referred to in the immediately preceding sentence, include all of the patents, patent applications, patent publications, and other documents cited anywhere in the present application.

Words relating to the opinions and judgments of the author of all patents, patent applications, patent publications, and other documents cited herein and not directly relating to the technical details of the description of the exemplifications therein are not incorporated by reference.

The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the abovementioned words in this sentence, when not used to describe technical features of one or more exemplifications of the patents, patent applications, patent publications, and other documents, are not considered to be incorporated by reference herein for any of the patents, patent applications, patent publications, and other documents cited herein.

The description of the exemplification or exemplifications is believed, at the time of the filing of this patent application, to adequately describe the exemplification or exemplifications of this patent application. However, portions of the description of the exemplification or exemplifications may not be completely applicable to the claims as originally filed in this patent application, as amended during prosecution of this patent application, and as ultimately allowed in any patent issuing from this patent application. Therefore, any statements made relating to the exemplification or exemplifications are not intended to limit the claims in any manner and should not be interpreted as limiting the claims in any manner.

The details in the patents, patent applications, patent publications, and other documents cited herein may be considered to be incorporable, at applicant's option, into the claims during prosecution as further limitations in the claims to patentably distinguish any amended claims from any applied prior art. The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the exemplification or exemplifications, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. § 1.72(b). As stated in 37 C.F.R. § 1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The exemplifications of the invention described herein above in the context of the preferred exemplifications are not to be taken as limiting the exemplifications of the invention to all of the provided details thereof, since modifications and variations thereof may be made without departing from the spirit and scope of the exemplifications of the invention.

What is claimed is:

1. A beverage bottle handling arrangement comprising:
a beverage bottle inlet configured to feed beverage bottles into the beverage bottle handling arrangement;
said beverage bottle inlet comprising a transport device comprising at least one of:
a rotatable carousel configured and disposed to hold beverage bottles on the perimeter thereof, and configured to move beverage bottles by rotating movement; and
a linear conveyor belt configured and disposed to hold beverage bottles thereon, and configured to move beverage bottles by linear movement;
at least one beverage bottle handling machine comprising a beverage bottle filling machine, a beverage bottle closing machine, and/or a beverage bottle labeling machine configured to fill, close, and/or label beverage bottles;
said beverage bottle handling machine comprising a transport device comprising at least one of:
a rotatable carousel configured and disposed to hold beverage bottles on the perimeter thereof, and configured to move beverage bottles by rotating movement; and
a linear conveyor belt configured and disposed to hold beverage bottles thereon, and configured to move beverage bottles by linear movement;
a beverage bottle checking arrangement being configured to check beverage bottles;
said beverage bottle checking arrangement comprising a single framework and at least four checking devices mounted on said framework, which said at least four checking devices are configured to essentially simultaneously check at least four characteristics of beverage bottles;
said beverage bottle checking arrangement comprising a transport device comprising at least one of:
a rotatable carousel configured and disposed to hold beverage bottles on the perimeter thereof, and configured to move beverage bottles by rotating movement; and
a linear conveyor belt configured and disposed to hold beverage bottles thereon, and configured to move beverage bottles by linear movement;
said transport device of said beverage bottle checking arrangement being configured and disposed to transport beverage bottles through or past said framework of said beverage bottle checking arrangement;
a beverage bottle outlet configured to feed beverage bottles out of the beverage bottle handling arrangement; and
said beverage bottle outlet comprising a transport device comprising at least one of:
a rotatable carousel configured and disposed to hold beverage bottles on the perimeter thereof, and configured to move beverage bottles by rotating movement; and a linear conveyor belt configured and disposed to hold beverage bottles thereon, and configured to move beverage bottles by linear movement.

2. A beverage bottle handling arrangement comprising:
a beverage bottle inlet configured to feed beverage bottles into the beverage bottle handling arrangement;
said beverage bottle inlet comprising a transport device comprising at least one of:
  a rotatable carousel configured and disposed to hold beverage bottles on the perimeter thereof, and configured to move beverage bottles by rotating movement; and
  a linear conveyor belt configured and disposed to hold beverage bottles thereon, and configured to move beverage bottles by linear movement;
at least one beverage bottle handling machine comprising a beverage bottle filling machine, a beverage bottle closing machine, and/or a beverage bottle labeling machine configured to fill, close, and/or label beverage bottles;
said beverage bottle handling machine comprising a transport device comprising at least one of:
  a rotatable carousel configured and disposed to hold beverage bottles on the perimeter thereof, and configured to move beverage bottles by rotating movement; and
  a linear conveyor belt configured and disposed to hold beverage bottles thereon, and configured to move beverage bottles by linear movement;
a beverage bottle checking arrangement being configured to check beverage bottles;
said beverage bottle checking arrangement comprising a single framework and at least three checking devices mounted on said framework, which said at least three checking devices are configured to essentially simultaneously check at least three characteristics of beverage bottles;
said beverage bottle checking arrangement comprising a transport device comprising at least one of:
  a rotatable carousel configured and disposed to hold beverage bottles on the perimeter thereof, and configured to move beverage bottles by rotating movement; and
  a linear conveyor belt configured and disposed to hold beverage bottles thereon, and configured to move beverage bottles by linear movement;
said transport device of said beverage bottle checking arrangement being configured and disposed to transport beverage bottles through or past said framework of said beverage bottle checking arrangement;
a beverage bottle outlet configured to feed beverage bottles out of the beverage bottle handling arrangement; and
said beverage bottle outlet comprising a transport device comprising at least one of:
  a rotatable carousel configured and disposed to hold beverage bottles on the perimeter thereof, and configured to move beverage bottles by rotating movement; and
  a linear conveyor belt configured and disposed to hold beverage bottles thereon, and configured to move beverage bottles by linear movement.

3. A beverage bottle checking arrangement being configured to check beverage bottles in a beverage bottle handling arrangement, which beverage bottle handling arrangement comprises a beverage bottle inlet configured to feed beverage bottles into the beverage bottle handling arrangement; at least one beverage bottle handling machine comprising a beverage bottle filling machine, a beverage bottle closing machine, and/or a beverage bottle labeling machine configured to fill, close, and/or label beverage bottles; and a beverage bottle outlet configured to feed beverage bottles out of the beverage bottle handling arrangement; wherein:
  said beverage bottle checking arrangement comprising a single framework and at least three checking devices mounted on said framework, which said at least three checking devices are configured to essentially simultaneously check at least three characteristics of beverage bottles.

4. The beverage bottle checking arrangement according to claim 3, wherein said at least three checking devices are mounted on said framework in positions to permit essentially simultaneous checking of at least three different characteristics of beverage bottles, which characteristics comprise a tamperproof security element on a beverage bottle closure, the contents of the beverage bottle, a closure logo on a beverage bottle closure, a code on the beverage bottle, and a beverage bottle label.

5. The beverage bottle checking arrangement according to claim 4, wherein the beverage bottle checking arrangement comprises a beverage bottle transport to move beverage bottles into a checking position of said beverage bottle checking arrangement to permit essentially simultaneous checking of at least three different characteristics of beverage bottles.

6. The beverage bottle checking arrangement according to claim 5, wherein said at least three checking devices comprise cameras and/or sensors.

7. The beverage bottle checking arrangement according to claim 6, wherein said beverage bottle transport is disposed to run through said framework.

8. The beverage bottle checking arrangement according to claim 7, wherein the beverage bottle checking arrangement comprises a lighting arrangement, which said lighting arrangement comprises at least two of:
  a ring lighting unit disposed above said beverage bottle transport, and oriented to illuminate a circumferential surface portion of a top of a beverage bottle in the checking position;
  a transmission lighting unit disposed offset from and on a first side of said beverage bottle transport, and oriented to illuminate a body portion and/or the contents of a beverage bottle in the checking position; and
  a direct lighting unit disposed offset from and on a second side of said beverage bottle transport, and oriented to illuminate a code and/or a label on a side surface portion of a beverage bottle in the checking position.

9. The beverage bottle checking arrangement according to claim 8, wherein:
  said direct lighting unit comprises two lighting bodies spaced apart from one another; and
  said transmission lighting unit comprises a flat lighting body.

10. The beverage bottle checking arrangement according to claim 9, wherein at least one of said checking devices comprises at least one mirror element configured to reflect light emitted from at least one of said lighting units to at least one of said cameras.

11. The beverage bottle checking arrangement according to claim 10, wherein:
  at least one of said cameras is disposed in an upper position above said beverage bottle transport; and
  at least one of said cameras is disposed in a lower position next to or below said beverage bottle transport.

12. The beverage bottle checking arrangement according to claim 11, wherein said cameras, said lighting units, and said mirror elements are disposed in different positions essentially above, below, and to the sides of a beverage bottle in the checking position to essentially surround the beverage bottle to minimize the overall volume of space occupied by the beverage bottle checking arrangement.

13. The beverage bottle checking arrangement according to claim 12, wherein said at least three checking devices comprise at least four checking devices to essentially simultaneously check at least four characteristics of beverage bottles.

14. The beverage bottle checking arrangement according to claim 13, wherein said at least four checking devices comprise at least five checking devices to essentially simultaneously check at least five characteristics of beverage bottles.

15. The beverage bottle checking arrangement according to claim 3, wherein said at least three checking devices comprise at least four checking devices to essentially simultaneously check at least four characteristics of beverage bottles.

16. The beverage bottle checking arrangement according to claim 3, wherein said at least three checking devices comprise at least five checking devices to essentially simultaneously check at least five characteristics of beverage bottles.

* * * * *